(12) United States Patent
Akiyama

(10) Patent No.: US 10,687,970 B2
(45) Date of Patent: Jun. 23, 2020

(54) ASSISTANCE DEVICE, ASSISTANCE GARMENT, AND ASSISTANCE METHOD

(71) Applicant: R.U. Technologies, Inc., Tokyo (JP)

(72) Inventor: Shoichi Akiyama, Tokyo (JP)

(73) Assignee: R.U. TECHNOLOGIES, INC., Tokyo (JP)

( * ) Notice: Subject to any disclaimer, the term of this patent is extended or adjusted under 35 U.S.C. 154(b) by 198 days.

(21) Appl. No.: 15/534,246

(22) PCT Filed: Nov. 20, 2015

(86) PCT No.: PCT/JP2015/082675
§ 371 (c)(1),
(2) Date: Jun. 8, 2017

(87) PCT Pub. No.: WO2016/093038
PCT Pub. Date: Jun. 16, 2016

(65) Prior Publication Data
US 2017/0340468 A1  Nov. 30, 2017

(30) Foreign Application Priority Data

Dec. 11, 2014  (JP) ................. 2014-251352

(51) Int. Cl.
*A61F 5/01* (2006.01)
*A61F 2/58* (2006.01)
*A61H 1/02* (2006.01)
*A61H 3/00* (2006.01)
*B25J 9/00* (2006.01)

(52) U.S. Cl.
CPC .............. *A61F 5/0102* (2013.01); *A61F 2/58* (2013.01); *A61H 1/0292* (2013.01); *A61H 3/008* (2013.01);
(Continued)

(58) Field of Classification Search
CPC .......... A61H 3/00; A61H 3/008; A61H 1/024; A61H 1/0244; A61F 5/028; A61F 5/01;
(Continued)

(56) References Cited

U.S. PATENT DOCUMENTS 4,841,845 A  6/1989 Beullens
7,299,741 B2 * 11/2007 Hiramatsu ........... A61H 1/0237
601/5
(Continued)

FOREIGN PATENT DOCUMENTS

JP  H02-167690 A  6/1990
JP  2006-000294 A1  1/2006
(Continued)

OTHER PUBLICATIONS

International Search Report for International Application No. PCT/JP2015/082675 dated Feb. 23, 2016.
(Continued)

*Primary Examiner* — Suba Ganesan
*Assistant Examiner* — Aren Patel
(74) *Attorney, Agent, or Firm* — Kratz, Quintos & Hanson, LLP

(57) ABSTRACT

Provided are an assistance device, an assistance garment, and an assistance method that enable easy replacement of a part of structure, suppression of fatigue of a wearer, and reduction of a load in an action of the wearer, without requiring time and effort for putting on and taking off. An assistance device 1 is provided on a garment and reduces a load in an action of a wearer 5. The assistance device 1 is provided with an assisting part 10 that is replaceable and applies force for assisting the an action to the body of the wearer 5 by changing flexibility, and an assist-control part 12 that controls the flexibility.

17 Claims, 15 Drawing Sheets

(52) U.S. Cl.
CPC ..... *B25J 9/0006* (2013.01); *A61H 2201/1246* (2013.01); *A61H 2201/1409* (2013.01); *A61H 2201/1623* (2013.01); *A61H 2201/5069* (2013.01); *A61H 2201/5071* (2013.01); *A61H 2203/0406* (2013.01)

(58) Field of Classification Search
CPC .......... A61F 5/012; A61F 5/03; A61F 5/0102; A61F 2/68; A61F 2/74; B25J 9/0006; A61G 1/024; A61G 1/0244
USPC .......... 601/5, 84; 602/16, 19, 26; 623/26, 30
See application file for complete search history.

(56) References Cited

U.S. PATENT DOCUMENTS

| | | | |
|---|---|---|---|
| 2010/0063601 A1* | 3/2010 | Sankai | A61H 1/0237 623/25 |
| 2011/0166491 A1 | 7/2011 | Sankai | |
| 2016/0252110 A1* | 9/2016 | Galloway | A61B 34/70 60/327 |

FOREIGN PATENT DOCUMENTS

| | | | | |
|---|---|---|---|---|
| JP | WO2007/058327 | * | 5/2007 | .............. F15B 15/10 |
| JP | 2010-070364 A1 | | 4/2010 | |
| JP | 5017660 B2 | | 9/2012 | |
| JP | 2013-022296 A1 | | 2/2013 | |
| WO | 2007/058327 A1 | | 5/2007 | |

OTHER PUBLICATIONS http://unsw.adfa.edu.au/school-of-engineering-and-information-technology/nonlinear-modelling-and-analysis-composite-pipes-offshore-oil-and-gas-applications; "Nonlinear modelling and analysis of composite pipes for offshore oil and gas applications"; Dec. 9, 2015; School of Engineering and Information Technology; UNSW Australian Defense Force Academy (3 sheets).

* cited by examiner

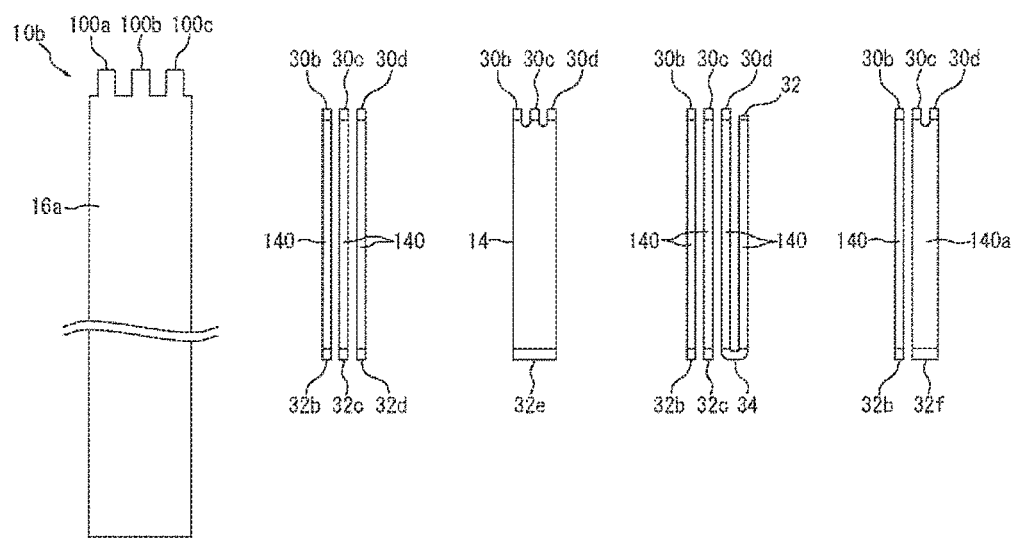

100

ASSISTANCE DEVICE, ASSISTANCE GARMENT, AND ASSISTANCE METHOD

TECHNICAL FIELD

The present invention relates to an assistance device, an assistance garment, and an assistance method. The present invention particularly relates to an assistance device, an assistance garment, and an assistance method for reducing a load in an action of a wearer and has structure in which a member composing the assistance device is replaceable.

BACKGROUND ART

In the conventional art, there is known a device for reducing a load on a waist, which has a waist belt attached to a position of a pelvis, elbow belts attached to positions of elbow joints, a support means fixed and held by the waist belt and extended to near shoulder positions, and tension means each of which provided between an upper part of this support means and the elbow belt (e.g., see Patent Literature 1). The device for reducing a load on a waist is configured such that the load received by the elbow belts is transmitted to the waist belt via the tension means and via the support means. The device for reducing a load described in Patent Literature 1 can reduce a burden on a backbone of a caregiver or a transportation worker.

CITATION LIST

Patent Literature

Patent Literature 1: JP 2010-70364 A

SUMMARY OF INVENTION

Technical Problem

The device for reducing a load described in Patent Literature 1, however, requires time and effort for putting on and taking off the device, and an outer surface of the device for reducing a load may come into contact with a care-receiver, or items around a caregiver. Furthermore, when a part composing the device for reducing a load is worn out, it is not easy to replace only the worn out part. Moreover, in the device for reducing a load described in Patent Literature 1, the belts and the like apply force to a part of a body, thereby to lift other parts of the body, causing great fatigue to the wearer.

Accordingly, an object of the present invention is to provide an assistance device, an assistance garment, and an assistance method that enable easy replacement of a part of configuration, suppression of fatigue of a wearer, and reduction of a load in an action of the wearer, without requiring time and effort for putting on and taking off.

Solution to Problem

To achieve the object above, the present invention provides an assistance device that is provided on a garment and reduces a load in an action of a wearer. The assistance device includes an assisting part that is replaceable and applies force for assisting the action to the body of the wearer by changing flexibility, and an assist-control part that controls the flexibility.

Additionally, in the above-described assistance device, the assisting part can have a first cylindrical part through which fluid flows in and out, and a second cylindrical part disposed with the first cylindrical part inside, and the assist-control part can also control the flexibility of the assisting part by changing fluid pressure in the first cylindrical part.

Additionally, in the above-described assistance device, the second cylindrical part can have higher longitudinal flexibility than radial flexibility, and the assist-control part can increase pressure in the first cylindrical part by pressurizing the fluid, and reduce the flexibility of the assisting part.

Additionally, the above-described assistance device can further include a receiving part that is provided inside the second cylindrical part, between an end part of the second cylindrical part and an end part of the first cylindrical part.

Additionally, in the above-described assistance device, at least a part of the second cylindrical part may be formed from a material with lower flexibility than the first cylindrical part.

Additionally, the above-described assistance device can further include, between the assist-control part and the first cylindrical part, a state-setting part that sets a state of pressure in the first cylindrical part to a plurality of states.

Additionally, in the above-described assistance device, the second cylindrical part can have, on a part of the second cylindrical part in a circumferential direction, an expansion/contraction limiting part that limits axial expansion/contraction of the second cylindrical part.

Additionally, in the above-described assistance device, the fluid is preferably incompressible fluid.

Additionally, the above-described assistance device can further include a replacement-time output part that outputs that the assisting part has reached its replacement time or may reach the replacement time within a prescribed period, when a degree of deterioration of the assisting part, which is determined in accordance with a number of times that the flexibility of the assisting part has been change by the assist-control part, has reached a predetermined reference, or when the degree of deterioration is included within a prescribed range from the predetermined reference.

Additionally, in the above-described assistance device, the replacement-time output part can include a replacement-time transmission part that transmits time information indicating that the replacement time has been reached, or may be reached within a prescribed period.

Further, to achieve the object above, the present invention provides an assistance garment including, on a back portion, an assistance device described in any one of the above. The assistance garment includes a holding part that is inserted with a first-end side of the assisting part and holds the first-end side movably along a longitudinal direction of the back portion, and a fixing part that detachably/attachably fixes at least a part of the assisting part other than the first-end side, to the assistance garment.

Additionally, in the above-described assistance garment, the fixing part can also detachably/attachably fix a second-end side of the assisting part at a position of a knee portion or higher, of the assistance garment.

Additionally, in the above-described assistance garment, the fixing part can also cover at least a part of the assisting part.

Further, to achieve the object above, the present invention provides an assistance method for operating an assistance device that is provided on a garment and reduces a load in an action of a wearer. The assistance method includes an assist-control step for controlling flexibility of an assisting part that is replaceable and applies force for assisting the action to the body of the wearer by changing the flexibility.

Additionally, in the above-described assistance method, the assisting part can have a first cylindrical part through which fluid flows in and out, and a second cylindrical part disposed with the first cylindrical part inside, and the assist-control step can control the flexibility of the assisting part by changing fluid pressure in the first cylindrical part.

Additionally, in the above-described assistance method, the second cylindrical part can have higher longitudinal flexibility than radial flexibility, and in the assist-control step, pressure in the first cylindrical part can be increased by pressurizing the fluid, and the flexibility of the assisting part can be reduced.

Advantageous Effects of Invention

According to the assistance device, the assistance garment, and the assistance method of the present invention, there can be provided an assistance device, an assistance garment, and an assistance method that enable easy replacement of a part of structure, suppression of fatigue of the wearer, and reduction of a load in an action of the wearer, without requiring time and effort for putting on and taking off.

BRIEF DESCRIPTION OF DRAWINGS

FIGS. 5(a) to 5(e) are still other structural views of the assisting part according to the embodiment.

DESCRIPTION OF EMBODIMENTS

Embodiment

Figure 1A:
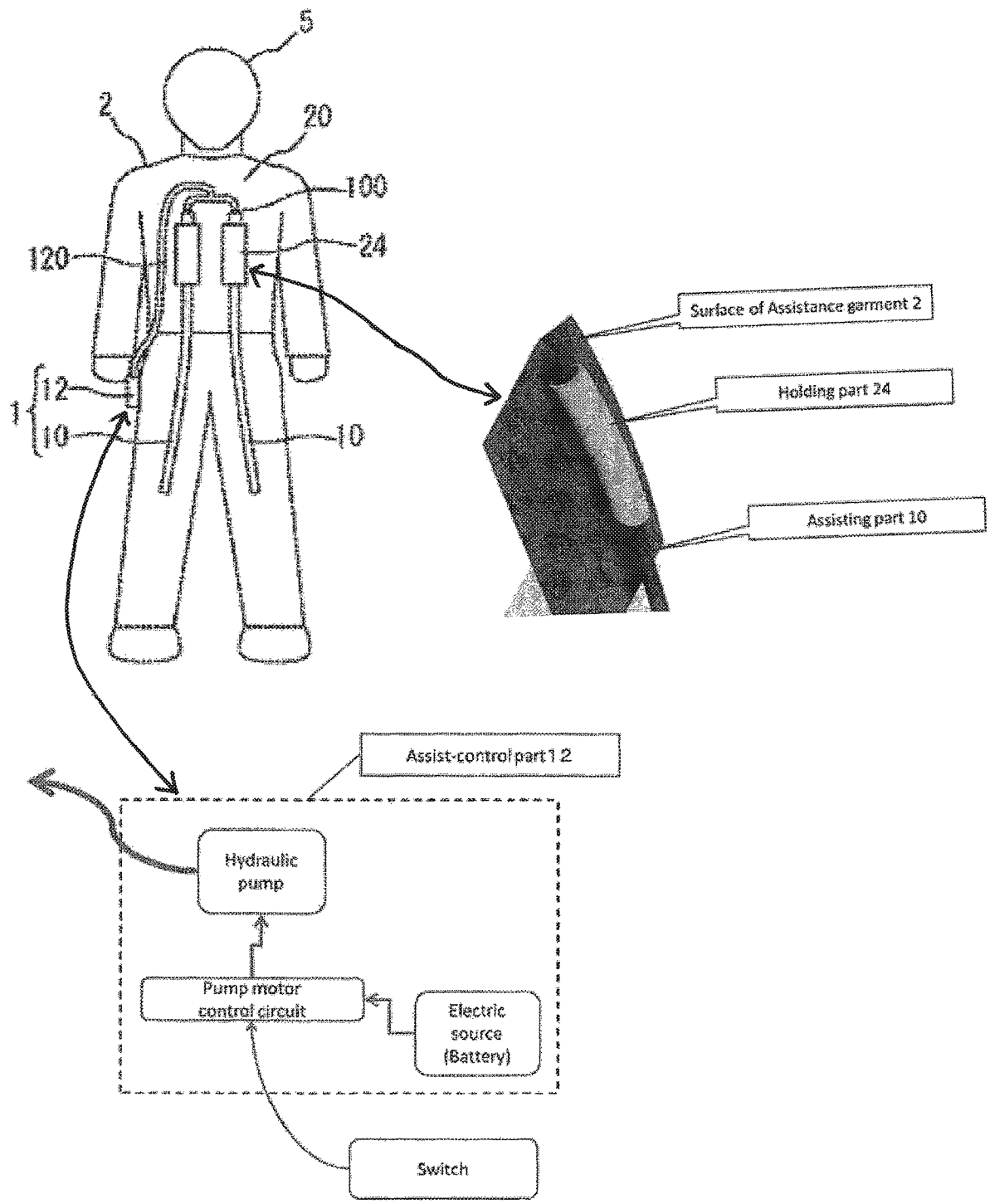
FIGS. 1(a) and 1(b) are outline views of an assistance device and an assistance garment according to this embodiment of the invention.
Figure 1B:
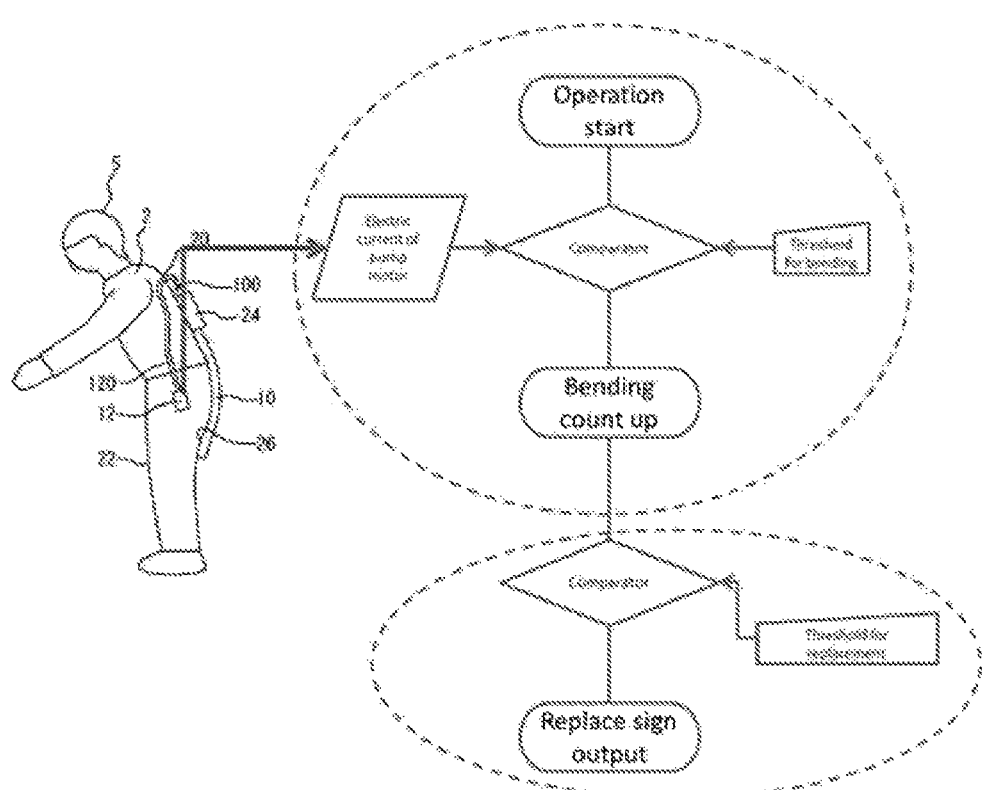

FIGS. 1(a) and 1(b) illustrate an outline of an assistance device and an assistance garment according to an embodiment of the present invention. To be more precise, FIG. 1(a) illustrates a back side of a wearer wearing an assistance device 1, and FIG. 1(b) illustrates a lateral side of the wearer.

[Summary of Assistance Device 1 and Assistance Garment 2]

The assistance device 1 according to the embodiment is a device that is provided on a garment and reduces a load in an action of a wearer 5. The assistance device 1 is a device that reduces a load in an action of a person who performs transportation or the like of a heavy object, a caregiver who takes care of a care-receiver, and/or a helper who assists a helped person, or the like, and the assistance device 1 is detachably/attachably provided on a garment. The assistance device 1 is, for example, provided corresponding to a part including a bent region of the body of the wearer 5, such as a lower back, knees, shoulders, and/or elbows, and reduces a load in an action of the wearer 5 in a bending action of the bent region, and/or a returning action to an original state from the bent state. The wearer 5 may also be a care-receiver and/or a helped person, and in this case, the assistance device 1 reduces a load in an action of the care-receiver and/or the helped person. Additionally, in this embodiment, a garment provided with the assistance device 1 is referred to as an assistance garment 2.

To be more precise, the assistance device 1 is provided in contact with a garment. The assistance device 1 includes an assisting part 10 that is provided so as to be removable and replaceable from the garment, and applies force for assisting an action of the wearer 5 to the body of the wearer 5 by changing its flexibility, and an assist-control part 12 that controls the flexibility of the assisting part 10. In this embodiment, as an example, it is explained that a case in which the assistance device 1 is used as a device for reducing a load in an action of the lower back of the wearer. In this case, the assistance device 1 is provided to a back portion 20, which is a back surface of the assistance garment 2.

First, the assistance garment 2 includes a holding part 24 that is provided on the back portion 20 and holds a first-end side of the assisting part 10, and a fixing part 26 that detachably/attachably fixes a second-end side of the assisting part 10 to the assistance garment 2. To be more precise, the assisting part 10 is provided along from the back portion 20 to a lower part of a thigh portion of the assistance garment 2 worn by the wearer 5. Moreover, a plurality of assisting parts 10 can be provided to the assistance garment 2. Then, the first-end side of the assisting part 10 is inserted into the holding part 24 that movably holds the assisting part 10 along a longitudinal direction of the back portion 20 over a predetermined length from a region including this first-end side toward the second-end side. In other words, the predetermined region from the first-end side toward the second-end side of the assisting part 10 is held movably with respect to the back portion 20.

Whereas, at least a part of the assisting part 10 other than the first-end side is fixed to the assistance garment 2 by the fixing part 26 that detachably/attachably fixes the part to the assistance garment 2. For example, the fixing part 26 detachably/attachably fixes a prescribed region including the second-end side of the assisting part 10 at a position of a knee portion 22 or higher, of the assistance garment 2. This can prevent the assistance device 1 from disturbing an action of the wearer 5, even when the wearer 5 bends his/her knee. Additionally, the first end of the assisting part 10 is provided with a connection port 100 that is connected to the assist-control part 12. The assist-control part 12 is, for example, detachably/attachably held by a lower back portion or the like of the assistance garment 2.

For example, the assisting part 10 is formed to have structure in which fluid flows in and out and fills inside, and the assist-control part 12 controls pressure of this fluid. In other words, while the assisting part 10 has the structure in which the fluid flows in and out on the first-end side where the connection port 100 is provided, the second-end side is sealed. Then, the assist-control part 12 controls flexibility of the assisting part 10 by allowing the fluid to flow in and out of the assisting part 10 via the connection port 100.

Here, the assisting part 10 is formed to have structure in which longitudinal flexibility of the assisting part 10 is higher than flexibility in a cross sectional direction of the assisting part 10. In other words, the assisting part 10 has the structure that reduces longitudinal flexibility (i.e., structure that increases hardness) due to the pressure transmitted in the longitudinal direction without substantially causing a shape change in the cross-sectional horizontal direction, even when pressure is applied in its cross-sectional horizontal direction. Consequently, when the assist-control part 12 pressurizes the fluid inside the assisting part 10, the pressure is applied along the longitudinal direction of the assisting part 10. Then, the assisting part 10 reduces the longitudinal flexibility in accordance with the internal pressurization, thereby to generate a driving force for changing from a flexible state to an inflexible linear state.

For example, in a state where the wearer 5 bends his/her lower back, the assist-control part 12 causes a state where the fluid inside the assisting part 10 is not pressurized. In this state, since the assisting part 10 is flexible, the wearer 5 can bend his/her lower back without feeling a load. Whereas, when the wearer 5 returns from the bent state of the lower back to an original state (straightened state) of the lower back, the assist-control part 12 pressurizes the fluid inside the assisting part 10. In this case, a driving force that shifts from the flexible state to the linear state arises in the assisting part 10. This driving force allows the assisting part 10 to reduce a load in the action of returning to the original state of the lower back of the wearer 5. This causes the assistance device 1 to generate a driving force corresponding to an action of the wearer 5, enabling reduction of a load in the action of the wearer 5.

Additionally, since the assisting part 10 according to the embodiment has a replaceable structure, even when the assisting part 10 is worn out due to bending or pressurization or the like, only the assisting part 10 can be easily replaced as one body.

[Detail of Assistance Device 1]

The assistance device 1 includes the assisting part 10 and the assist-control part 12. The assisting part 10 is configured to have one or a plurality of cylindrical parts, and the assist-control part 12 is configured to have a pressure-control part that allows fluid to flow in and out of at least one of the cylindrical parts composing the assisting part 10, thereby to control pressure in the cylindrical part. Further, the assisting part 10 and the assist-control part 12 are coupled by a connecting member 120. The connecting member 120, for example, serves as a passage through which fluid flows, and is configured by using a material endurable against pressurization of the assisting part 10. Moreover, the assist-control part 12 has a switch that performs pressurization or depressurization of the fluid. With a focus on a plurality of forms of the assisting part 10, each of the forms is described in detail below.

[Detail of Assisting Part 10]

FIGS. 2(*a*) and 2(*b*) illustrate one example of structure of the assisting part according to the embodiment. To be more precise, FIG. 2(*a*) is an example of a front face of the assisting part 10, and FIG. 2(*b*) is an example of an A-A cross section of FIG. 2(*a*).

In FIGS. 2(*a*) and 2(*b*), the assisting part 10 has, on a first end, the connection port 100 connected to the assist-control part 12, and has a substantially cylindrical shape with a second end 102 sealed. Additionally, the assisting part 10 is configured to have a first cylindrical part 14 in which fluid flows in and out from a first-end side and a second end is sealed, and a second cylindrical part 16 disposed with the first cylindrical part 14 inside. Here, at least a part of an outer surface of the first cylindrical part 14 is provided in contact with an inner surface of the second cylindrical part 16. Further, in FIGS. 2(*a*) and 2(*b*), in the assisting part 10, one first cylindrical part 14 is disposed inside the second cylindrical part 16.

The first cylindrical part 14 is configured such that fluid flows in and out of inside thereof. To be more precise, the connection port 100 is coupled to a first end of the first cylindrical part 14, and the fluid flows in and out of the first cylindrical part 14 from this first end. Additionally, the second end of the first cylindrical part 14 is sealed. Moreover, there can be provided a vent part that discharges bubbles contained in the fluid to outside, at the second end of the first cylindrical part 14 or a prescribed place of the first cylindrical part 14. Then, the assist-control part 12 controls flexibility of the assisting part 10 by changing pressure of the fluid in the first cylindrical part 14.

Here, the first cylindrical part 14 is mainly formed from a resin material such as an elastomer resin, and the second cylindrical part 16 is mainly formed from a resin material having higher hardness than that of the resin material forming the first cylindrical part 14, or a metallic material such as stainless steel. Then, the second cylindrical part 16 has structure in which longitudinal flexibility is higher than radial flexibility. Namely, the second cylindrical part 16 has structure that has high hardness and is hardly deformable in a radial direction. In other words, the second cylindrical part 16 has the structure in that, radial deformation is substantially not caused even when radial force is applied, whereas the second cylindrical part 16 is bent in a longitudinal direction, and the structure allows expansion and contraction to some extent. Moreover, at least a part of the second cylindrical part 16 can be formed by using a material having lower flexibility than that of the first cylindrical part 14.

As an example, the second cylindrical part 16 is a combination of a metal-member part configured by a metallic material and a resin-member part configured by a resin material, a combination of a metal-member part and a metal-member part (or a cylindrical metal member in which a thickness varies at a predetermined interval along a longitudinal direction), or a combination of a resin-member part and a resin-member part (or a cylindrical resin member in which a thickness varies at a predetermined interval along a longitudinal direction). The second cylindrical part 16 can be configured to include structure in which each combination part (or a thin part for a cylindrical member in which a thickness varies at predetermined interval along the longitudinal direction) has a predetermined movability (or a deformable property). For example, the second cylindrical part 16 can be configured to have a bellows structure. Moreover, it is preferable that an outflow/inflow port for fluid, which is provided at the first end of the first cylindrical part 14, is formed by using a material having higher hardness than at least that of a material forming other parts of the first cylindrical part 14.

Then, the assist-control part 12 increases pressure in the first cylindrical part 14 by pressurizing the fluid in the first cylindrical part 14, to apply pressure in a longitudinal direction of the second cylindrical part 16 (i.e., the pressure is transmitted along the longitudinal direction of the second cylindrical part 16, and the pressure is concentrated at an end part of the second cylindrical part 16). This reduces the longitudinal flexibility of the assisting part 10 (i.e., causes a driving force for shifting the assisting part 10 to a linear state), and generates a driving force for reducing a load in an action of the wearer 5. The assist control part 12 is, for example, configured to have, as the pressure-control part, a pump for liquid-pressure feeding, such as a small hydraulic-pump or a small liquid-feeding pump, that allows the fluid to flow in and out of the first cylindrical part 14. Additionally, it is preferable to use incompressible fluid, such as water, as the fluid in this embodiment. Moreover, it is preferable to use incompressible fluid that is safe to a human body. The incompressible fluid with ensured safety to a human body includes, for example, antifreeze composed of a component approved as a food additive, with propylene glycol (the chemical name: 1,2-propanediol) as a principal component. Moreover, as the incompressible fluid, there can be used various kinds of working fluid developed for hydraulic driving. For the purpose of preventing corrosion of a part in contact with the fluid of the assistance device 1, such a working fluid is preferably used. Further, the incompressible fluid can be added with rust preventive that is harmless to a human body. Since the assistance garment 2 provided with the assistance device 1 is in contact with the body of the wearer 5, safety to a human body can be ensured even in case of leakage of the fluid from assistance device 1.

Moreover, sectional shapes of the first cylindrical part 14, the second cylindrical part 16, and/or the assisting part 10 are not only circular, but can also be a polygonal shape or the like including an elliptic, square, rectangular, or triangle shape. For example, the first cylindrical part 14, the second cylindrical part 16, and/or the assisting part 10 can be configured as a tubular body having a cylindrical, rectangular tubular, or other shape.

Additionally, the assistance device 1 according to the embodiment may further include, between the assist-control part 12 and the first cylindrical part 14, a state-setting part that sets a state of pressure in the first cylindrical part 14 to a plurality of states. The state-setting part sets at least a first state where the assist-control part 12 continuously controls the pressure in the first cylindrical part 14, and a second state where the assist-control part 12 does not control the pressure in the first cylindrical part 14. For example, the state-setting part is a valve. As an example, when the valve is closed while the fluid in the first cylindrical part 14 is pressurized by the assist-control part 12, the fluid in the first cylindrical part 14 is maintained in a pressurized state (second state). On the other hand, in a state where the valve is opened, the assist-control part 12 can freely control the pressure of the fluid. In the first cylindrical part 14 (first state). At a time when the valve is closed, the pressure in the first cylindrical part 14 is maintained at a pressure at that time. Thus, the assist-control part 12 controls the pressure of the fluid in the first cylindrical part 14 to various pressures and closes the valve, which enables setting of a plurality of states. Additionally, the state-setting part can set a state through automatic control based on a posture of the wearer 5, or manually set a plurality of states. Further, the assist-control part 12 can also control operation of the state-setting part. For example, the assist-control part 12 performs control for switching between the first state and the second state of the state-setting part, as required. As an example, the assist-control part 12 controls the state-setting part based on a posture state or the like of a user, to switch between the first state and the second state.

When the valve is closed while the fluid in the first cylindrical part 14 is pressurized to some extent by the assist-control part 12, the assisting part 10 becomes in a state where the flexibility is reduced to some extent (the state of the pressure in the first cylindrical part 14 in this case is hereinafter referred to as a "third state"). In other words, in the third state, the assisting part 10 can continuously apply constant force to the wearer 5, without operation of the assist-control part 12. For example, in the third state, when the first cylindrical part 14 is bent, the pressure in the first cylindrical part 14 is increased depending on a degree of the bending. Therefore, in the third state, it is possible to reduce a load for light work such as when the wearer 5 slightly bends his/her lower back. In other words, in the third state, it is possible to support a load about a weight of the wearer 5, and in this case, operation of the assist-control part 12 is not required. Thus, the state-setting part can reduce energy consumption of the assistance device 1.

Figure 3A:
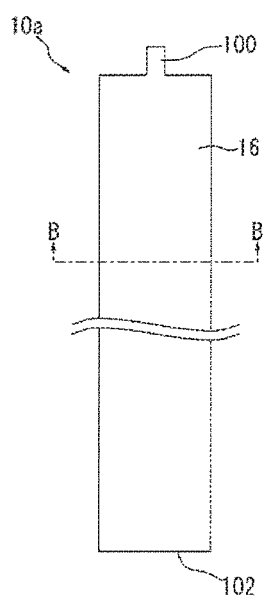
FIGS. 3(a) to 3(c) are other structural views of the assisting part according to the embodiment.
Figure 3B:
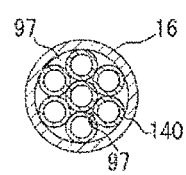
Figure 3C:
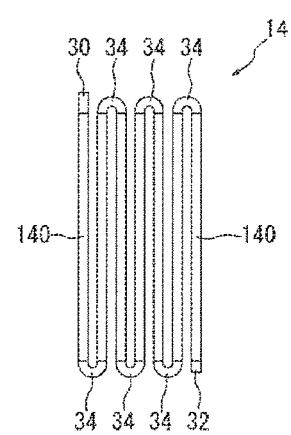

FIGS. 3(*a*) to 3(*c*) illustrate another example of structure of the assisting part according to the embodiment. To be more precise, FIG. 3(*a*) is an example of a front face of an assisting part 10*a*, and FIG. 3(*b*) is an example of a B-B cross section of FIG. 3(*a*). Additionally, FIG. 3(*c*) illustrates an example of a shape of the first cylindrical part 14.

The example in FIGS. 3(*a*) to 3(*c*) is different from the example in FIGS. 2(*a*) and 2(*b*) in that the first cylindrical part 14 is housed in a meandering state in the second cylindrical part 16. Therefore, in the description of the example in FIGS. 3(*a*) to 3(*c*), detailed description for a point having a substantially identical configuration and function to the example in FIGS. 2(*a*) and 2(*b*) is omitted, and only differences are described in detail.

First, in FIGS. 3(*a*) to 3(*c*), the first cylindrical part 14 is configured to include a plurality of thin-type cylindrical parts 140 having a smaller cross-sectional area than that of the first cylindrical part 14. To be more precise, in the example in FIGS. 3(*a*) to 3(*c*), the first cylindrical part 14 is configured by coupling the plurality of thin-type cylindrical parts 140 in series. Here, the plurality of thin-type cylindrical parts 140 are coupled to each other by a connection part 34. Then, there is provided an inlet 30 at a first end of one thin-type cylindrical part 140 connected to the connection port 100, and when the one thin-type cylindrical part 140 is defined as a foremost end among the serially coupled thin-type cylindrical parts 140, a sealing part 32 seals an end part of a thin-type cylindrical part 140 at a rearmost end, which is opposite to a side that is coupled to another thin-type cylindrical part 140. Moreover, the sealing part 32 can be provided with a vent part.

The first cylindrical part 114 configured by coupling the plurality of thin-type cylindrical parts 140 in series is folded and housed inside the second cylindrical part 16. In this case, each of the connection part 34, the inlet 30, and the sealing part 32, of the plurality of thin-type cylindrical parts 140, is arranged to be positioned at an end part of the second cylindrical part 16. The inlet 30, the sealing part 32, and/or the connection part 34 are formed by using a material having higher hardness than that of a material forming the thin-type cylindrical parts 140. For example, while the thin-type cylindrical parts 140 are mainly formed by a resin material such as an elastomer resin, each of the inlet 30, the sealing part 32, and the connection part 34 is formed by a resin material having higher hardness than that of the resin material forming the thin-type cylindrical parts 140, or a metallic material. This causes the pressure applied to the first cylindrical part 14 to be concentrated at the end part of the second cylindrical part 16.

Moreover, since the first cylindrical part 14 configured by coupling the plurality of thin-type cylindrical parts 140 is folded and housed inside the second cylindrical part 16, a gap 97 is formed in a part between the plurality of thin-type cylindrical parts 140, and a part between the thin-type cylindrical parts 140 and the second cylindrical part 16, as shown in the example of the cross section of FIG. 3(*b*). This causes a plurality of the gaps 97 to serve as an escape space for pressure when the fluid in the first cylindrical part 14 is pressurized, enabling an increase in flexibility of the entire assisting part 10.

(Detail of Other Structures of First Cylindrical Part 14)

Figure 4:
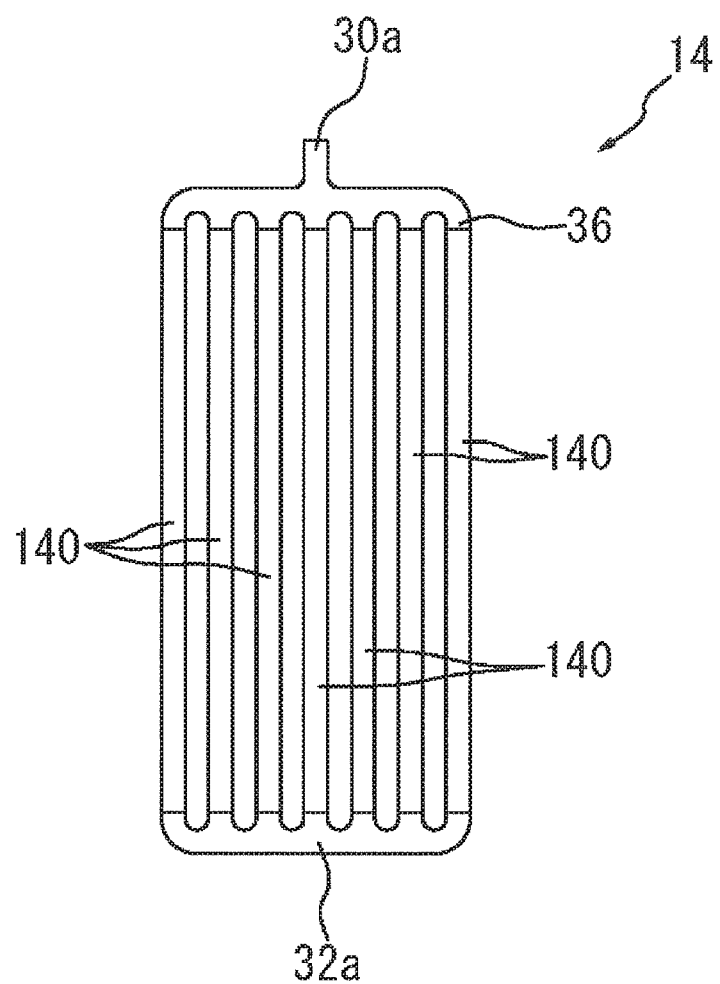
FIG. 4 is another structural view of a first cylindrical part according to the embodiment.

FIG. 4 illustrates another example of structure of the first cylindrical part according to the embodiment.

The example in FIG. 4 is different from the example in FIGS. 3 (*a*) to 3(*c*) in that the plurality of thin-type cylindrical parts 140 composing the first cylindrical part 14 are configured to be coupled in parallel. Therefore, in the description of the example in FIG. 4, detailed description for a point having a substantially identical configuration and function to the example in FIGS. 3(*a*) to 3(*c*) is omitted, and only differences are described in detail.

In the example in FIG. 4, the plurality of thin-type cylindrical parts 140 are connected with each other in parallel. To be more precise, each first end of the plurality of thin-type cylindrical parts 140 is connected to a parallel connection part 36 having an inlet 30*a* connected to the connection port 100. The parallel connection part 36 integrally connects the first ends of the plurality of thin-type cylindrical parts 140. On the other hand, each second end of the plurality of thin-type cylindrical parts 140 is integrally sealed by a sealing part 32*a*. The parallel connection part 36 and the sealing part 32*a* are formed by using a material having higher hardness than that of a material forming the thin-type cylindrical parts 140. Additionally, the parallel connection part 36 and the sealing part 32*a* are arranged to be positioned at the end parts of the second cylindrical part 16.

Connecting the plurality of thin-type cylindrical parts 140 in parallel allows improvement of pressure-transmission speed when the fluid in the first cylindrical part 14 is pressurized. This can improve response speed of the entire assisting part 10.

(Detail of Other Structures of Assisting Part 10)

FIGS. 5(*a*) to 5(*e*) illustrate still another example of structure of the assisting part according to the embodiment.

The example in FIGS. 5(*a*) to 5(*ef*) is different from the examples in FIGS. 2(*a*) and 2(*b*) to FIG. 4 in that a first end of an assisting part 10*b* is provided with a plurality of connection ports. Therefore, in the description of the example in FIGS. 5(*a*) to 5(*e*), detailed description for a point having a substantially identical configuration and function to the examples in FIGS. 2(*a*) and 2(*b*) to FIG. 4 is omitted, and only differences are described in detail.

First, FIG. 5(*a*) is referred. In FIG. 5(*a*), the assisting part 10*b* includes a plurality of first cylindrical parts, and a second cylindrical part 16*a* that has, on a first end, a plurality of the connection ports connected to the assist-control part 12 (for example, a connection port 100*a*, a connection port 100*b*, and a connection port 100*c*). For arrangement of the first cylindrical part in the second cylindrical part 16*a*, various arrangements can be adopted as shown in FIGS. 5(*b*) to 5(*e*).

As shown in FIG. 5(*b*), in one aspect of the embodiment, the first cylindrical part can be configured by the plurality of thin-type cylindrical parts 140, and each of the plurality of thin-type cylindrical parts 140 can be independently arranged in the second cylindrical part 16*a*. For example, a first end of one thin-type cylindrical part 140 is defined as an inlet 30*b*, and a second end is defined as a sealing part 32*b*. Then, the inlet 30*b* is coupled to the connection port 100*a*. Additionally, a first end of another thin-type cylindrical part 140 is defined as an inlet 30*c*, and a second end is defined as a sealing part 32*c*. Then, the inlet 30*c* is coupled to the connection port 100*b*. Additionally, a first end of still another thin-type cylindrical part 140 is defined as an inlet 30*d*, and a second end is defined as a sealing part 32*d*. Then, the inlet 30*d* is coupled to the connection port 100*c*. Each of the inlets 30*b* to 30*d* and the sealing parts 32*b* to 32*d* is formed by a material having higher hardness than that of the thin-type cylindrical parts 140, and arranged to be positioned at an end part of the second cylindrical part 16*a*. In the structure in which each of the plurality of thin-type cylindrical parts 140 is independently arranged. In the second cylindrical part 16*a*, even when internal pressure of any of the plurality of thin-type cylindrical parts 140 is decreased due to damage or the like, sudden loss of the driving force generated by the assisting part. 10 can be prevented since the other thin-type cylindrical parts 140 maintain the function.

Next, as shown in FIG. 5(*c*), in another aspect of the embodiment, it is possible to configure such that a first end of one first cylindrical part 14 is provided with a plurality of inlets (e.g., an inlet 30*b*, an inlet 30*c*, and an inlet 30*d*), and a second end is integrally sealed by a sealing part 32*e*. In this case, for example, the inlet 30*b* is coupled to the connection port 100*a*, the inlet 30*c* is coupled to the connection port 100*b*, and the inlet 30*d* is coupled to the connection port 100*c*. Each of the inlets 30*b* to 30*d* and the sealing part 32*e* is formed by a material having higher hardness than that of a thin-type cylindrical part 140, and arranged to be positioned at an end part of the second cylindrical part 16*a*.

Next, as shown in FIG. 5(*d*), in still another aspect of the embodiment, the first cylindrical part can be configured by the plurality of thin-type cylindrical parts 140, and a part of the thin-type cylindrical parts 140 can be coupled in series. Moreover, a part of the thin-type cylindrical parts 140 can also be coupled in parallel (not shown).

In other words, a first end of one thin-type cylindrical part 140 is defined as an inlet 30*b*, and a second end is defined as a sealing part 32*b*. Then, the inlet 30*b* is coupled to the connection port 100*a*. Additionally, a first end of another thin-type cylindrical part 140 is defined as an inlet 30*c*, and a second end is defined as a sealing part 32*c*. Then, the inlet 30*c* is coupled to the connection port 100*b*. Moreover, among the other plurality of thin-type cylindrical parts 140, a first end of one thin-type cylindrical part 140 is defined as an inlet 30*d*, and the plurality of thin-type cylindrical parts 140 are coupled in series by the connection part 34. Then, among the coupled thin-type cylindrical parts 140, when the thin-type cylindrical part 140 having the inlet 30*d* is defined as a thin-type cylindrical part 140 at a foremost end, the sealing part 32 seals an end on the other side of a side connected to another thin-type cylindrical part 140, of a thin-type cylindrical part 140 at a rearmost end. The inlet 30*d* is coupled to the connection port 100*c*.

Moreover, as shown in FIG. 5(e), in still another aspect of the embodiment, the first cylindrical part can be configured by using a plurality of thin-type cylindrical parts having cross-sectional areas different from each other. For example, the cylindrical part can be configured to have a thin-type cylindrical part 140, and a thin-type cylindrical part 140a having a larger cross-sectional area than that of this thin-type cylindrical part 140. In this case, a first end of the thin-type cylindrical part 140 is defined as an inlet 30b, and a second end is defined as a sealing part 32b. Additionally, a first end of the thin-type cylindrical part 140a is provided with a plurality of inlets (e.g., an inlet 30c and an inlet 30d), and a second end is provided with a sealing part 32f that integrally seals the second end. The inlet 30b is coupled to the connection port 100a, and the inlet 30c and the inlet 30d are respectively coupled to the connection port 100b and the connection port 100c. Moreover, the first cylindrical part can be configured to have a thin-type cylindrical part 140, and a thin-type cylindrical part having a smaller cross-sectional area than that of this thin-type cylindrical part 140.

(Detail of Shape of Second Cylindrical Part)

Figure 6A:
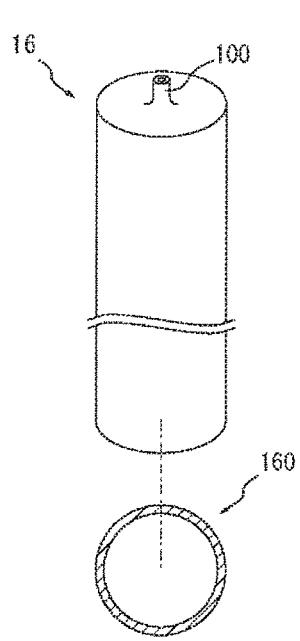
FIGS. 6(a) to 6(c) are views of a shape of a second cylindrical part according to the embodiment.
Figure 6B:
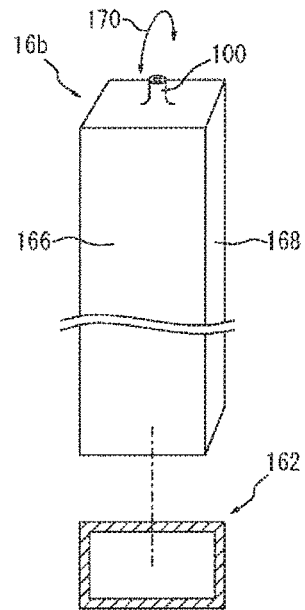
Figure 6C:
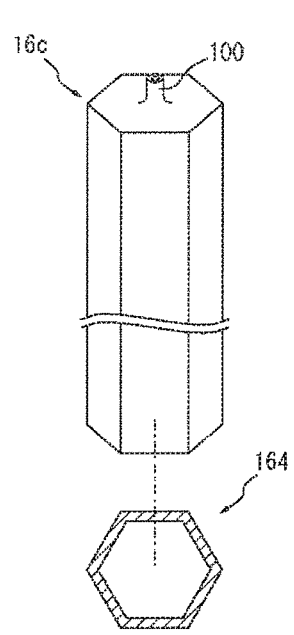

FIGS. 6(a) to 6(c) Illustrate examples of a shape of the second cylindrical part according to the embodiment. To be more precise, an upper part of FIGS. 6(a) to 6(c) illustrates a perspective example of the second cylindrical part, and a lower part illustrates a cross-sectional example.

The second cylindrical part can be in various kinds of shapes as long as it has a space for housing the first cylindrical part inside. For example, the second cylindrical part 16 shown in FIG. 6(a) has a substantially cylindrical shape with a circular cross section 160. Additionally, a second cylindrical part 16b shown in FIG. 6(b) has a substantially prismatic shape with a rectangular cross section 162. Moreover, the second cylindrical part 16b can be in a columnar shape having a square or diamond sectional shape. Further, a second cylindrical part 16c shown in FIG. 6(c) has a substantially columnar shape with a polygonal cross section 164.

Here, the second cylindrical part 16b has the rectangular crass section 162. In this case, when pressure is applied to the fluid in the first cylindrical part 14, a driving force is generated in a specific direction n the second cylindrical part 16b. In other words, when a front face 166 corresponding to a long side and a side face 168 corresponding to a short side are defined at the cross section of the second cylindrical part 16b, the assisting part 10 is driven corresponding to a direction along the front face 166 to its opposite face, or the opposite face to the front face 166 (direction of an arrow 170 in FIG. 6(b)). Moreover, when the sectional shape of the second cylindrical part 16b is made to be a square shape, a bending direction of the assisting part 10 can be limited to two directions, from one face to its opposite face, and from a face next to this one face to an opposite face of this face next to the one face. Consequently, when reduction of a load in an action of the wearer 5 by the assisting part 10 is limited to a specific direction, the second cylindrical part 16b preferably has a substantially rectangular or substantially square sectional shape.

Figure 7A:
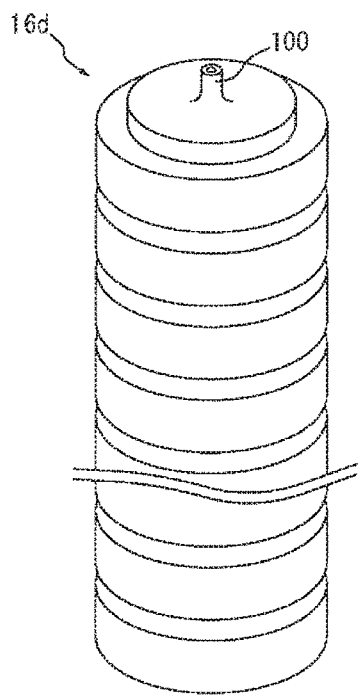
FIGS. 7(a) and 7(b) are other views of a shape of the second cylindrical part according to the embodiment.
Figure 7B:
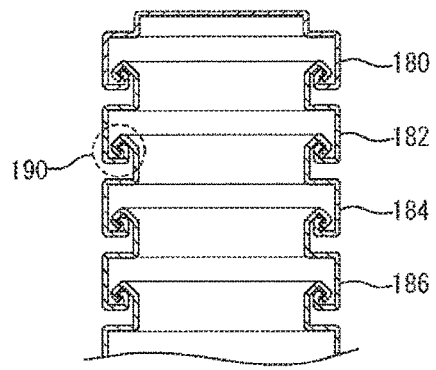

FIGS. 7(a) and 7(b) illustrate another example of a shape of the second cylindrical part according to the embodiment.

A second cylindrical part 16d can also be structured to couple a plurality of small cylindrical parts (e.g., a small cylindrical part 180, a small cylindrical part 182, a small cylindrical part 184, a small cylindrical part 186 and the like) having a short cylindrical shape formed from a thin plate. Each of the plurality of small cylindrical parts has a cylindrical portion, and a coupling part that is, provided on an edge of the cylindrical portion and coupled to another small cylindrical part. Each of the plurality of small cylindrical parts is, for example, formed from a metallic material such as stainless steel. One small cylindrical part, and another small cylindrical part that is coupled to the one small cylindrical part are coupled to each other through the coupling part. Then, the coupling of the one small cylindrical part and the another small cylindrical part gives prescribed flexibility to the second cylindrical part 16d, forming a combination part 190 having a prescribed spatial allowance in a longitudinal direction. As the second cylindrical part 16d, for example, a flexible tube made of stainless steel is available.

Figure 8:
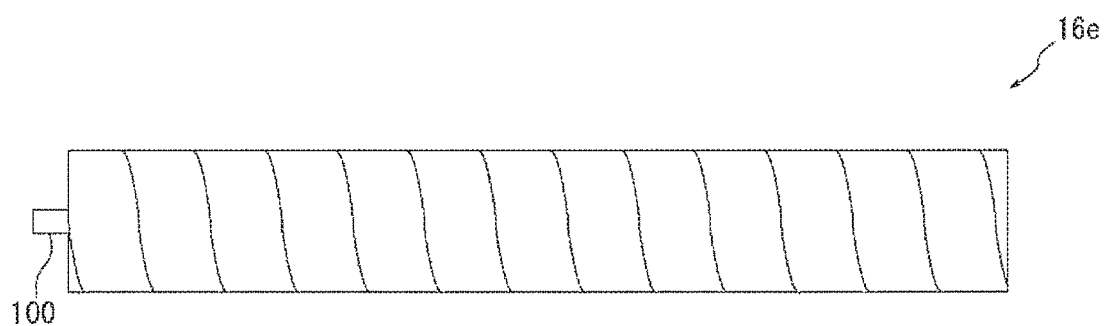
FIG. 8 is still another view of a shape of the second cylindrical part according to the embodiment.

FIG. 8 illustrates still another example of a shape of the second cylindrical part according to the embodiment.

A second cylindrical part 16e has a spiral tube structure that can be easily bent. In other words, the second cylindrical part 16e is formed by winding a thin-plate member having a prescribed width. Forming the second cylindrical part 16e into the spiral tube structure realizes easy manufacturing of the second cylindrical part 16e, and reduction of manufacturing cost. Further, the second cylindrical part 16e can be formed, for example, by using a metallic material such as stainless steel, aluminum alloy, titanium, and/or titanium alloy. Moreover, a surface of the second cylindrical part 16e can be covered by a resin material such as polyvinyl chloride.

(Other Internal Structures of Assisting Part)

Figure 9:
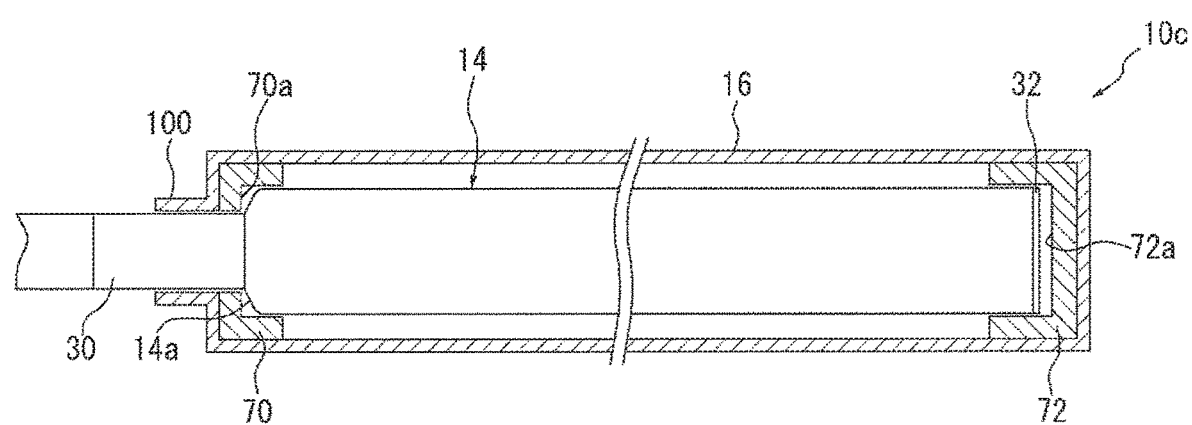
FIG. 9 is an outline view of another internal structure of the assisting part according to the embodiment.

FIG. 9 illustrates an example of an outline of another internal structure of the assisting part according to the embodiment.

Figure 2A:
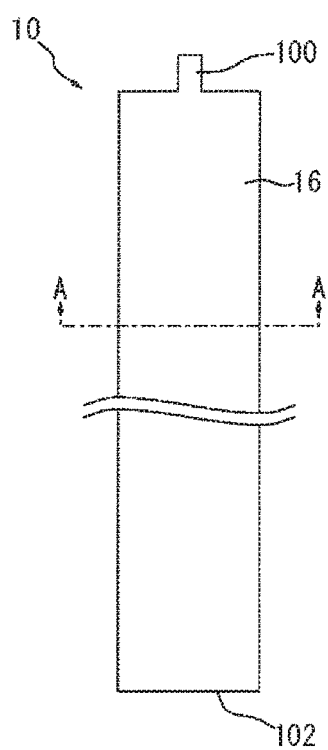
FIGS. 2(a) and 2(b) are structural views of an assisting part according to the embodiment.
Figure 2B:
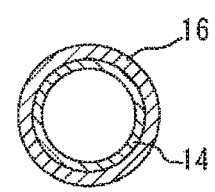

The example in FIG. 9 is different from the example in FIGS. 2(a) and 2(b) in that a receiving part 70 and a receiving part 72 are provided inside the second cylindrical part 16. Therefore, in the description of FIG. 9, detailed description for a point having a substantially identical configuration and function to the example in FIGS. 2(a) and 2(b) is omitted, and only differences are described in detail.

In an assisting part 10c shown in FIG. 9, the second cylindrical part 16 has the receiving part 70 at a first end part inside. Additionally, the second cylindrical part 16 has the receiving part 72 at a second end part inside. In other words, each of the receiving part 70 and the receiving part 72 is provided between each end part inside the second cylindrical part 16, and each end part of the first cylindrical part 14.

When fluid inside the first cylindrical part 14 is pressurized, and the first cylindrical part 14 is extended, a first end part 14a of the first cylindrical part 14 comes into contact with a contact part 70a of the receiving part 70. Similarly, the sealing part 32 at the second end part of the first cylindrical part 14 comes into contact with a contact part 72a of the receiving part 72. In other words, when the fluid inside the first cylindrical part 14 is pressurized, the first cylindrical part 14 extends in a longitudinal direction. When the first cylindrical part 14 extends in the longitudinal direction, both the end parts of the first cylindrical part 14 respectively come into contact with the end parts inside the second cylindrical part 16, applying pressure in a longitudinal direction of the second cylindrical part 16. In this case, the receiving part 70 and the receiving part 72 receive pressure concentrated at the end parts of the second cylindrical part 16, and efficiently generate a driving force of the assisting part 10c.

Moreover, the receiving part 70 and/or the receiving part 72 may be respectively in contact with or fixed to the end parts of the first cylindrical part 14. More particularly, the first end part 14a of the first cylindrical part 14 may previously be in contact or fixed to the contact part 70a of the receiving part 70. Similarly, the sealing part 32 at the second end part of the first cylindrical part 14 may previously be in contact or fixed to the contact part 72a of the receiving part 72. Also in this case, when the fluid inside the first cylindrical part 14 is pressurized, the end parts of the first cylindrical part 14 applies pressure to the receiving part 70 and/or the receiving part 72. Then, the receiving part 70 and/or the receiving part 72 receive this pressure, and efficiently generate a driving force of the assisting part 10c.

Each of the receiving part 70 and the receiving part 72 is fixed to the second cylindrical part 16 by adhesive or connecting member such as a screw. Moreover, each of the receiving part 70 and the receiving part 72 can partially have a screw shape. In this case, the receiving part 70 and the receiving part 72 are screwed to the second cylindrical part 16. Further, each of the receiving part 70 and the receiving part 72 is mainly formed by a resin material such as a polyacetal, or a metallic material such as stainless steel, aluminum alloy, titanium, and/or titanium alloy. Each of the receiving part 70 and the receiving part 72 is preferably formed from a light resin material, aluminum alloy or the like, when aiming at weight reduction of the assistance device 1. Note that materials forming the receiving part 70 and the receiving part 72 may be the same or different.

Additionally, each of the receiving part. 70 and the receiving part 72 can have a shape matching the end part of the first cylindrical part 14. Moreover, when the first cylindrical part 14 has the plurality of thin-type cylindrical parts 140, each of the receiving part 70 and the receiving part 72 can have a shape matching an end part of at least one thin-type cylindrical part 140.

Further, between the first cylindrical part 14 and the second cylindrical part 16, there can be provided a sleeve disposed at a position surrounding an outer circumference of the first cylindrical part 14. The sleeve has, for example, a seamless cylindrical shape. Moreover, the sleeve may be formed into a cylindrical shape by winding a sheet-like film around the outer circumference of the first cylindrical part 14. The sleeve can be formed by using a resin film or the like. Providing this sleeve between the first cylindrical part 14 and the second cylindrical part 16 enables improvement of sliding of an outer surface of the first cylindrical part 14 with respect to an inner surface of the second cylindrical part 16 when the assisting part 10 is bent, realizing smoother operation of the assisting part 10.

(Reinforcing Part 80)

Figure 10A:
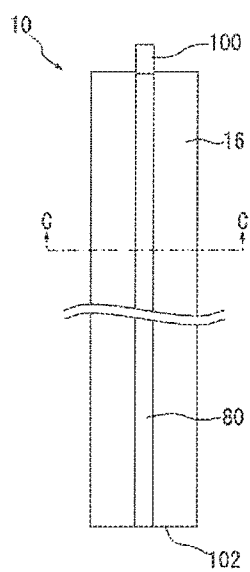
FIGS. 10(a) to 10(c) are outline views of the assisting part when having a reinforcing part, according to the embodiment.
Figure 10B:
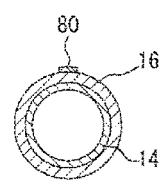
Figure 10C:
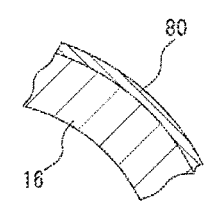

FIGS. 10(a) to 10(c) illustrate an example of an outline when the assisting part according to the embodiment has an expansion/contraction limiting part. To be more precise, FIG. 10(a) illustrates a front face of the second cylindrical part 16 having a reinforcing part 80 as the expansion/contraction limiting part, and FIG. 10(b) illustrates a cross section of the second cylindrical part 16 having the reinforcing part 80. Further, FIG. 10(cf) illustrates an example of a part of a state where the second cylindrical part 16 having the reinforcing part 80 is bent.

The examples in FIGS. 10(a) to 10(c) are different from the example in FIGS. 2(a) and 2(b) in that the reinforcing part 80 is provided as the expansion/contraction limiting part on a surface of the second cylindrical part 16. Therefore, in the description of FIGS. 10(a) to 10(c), detailed description for a point having a substantially identical configuration and function to the example in FIGS. 2(a) and 2(b) is omitted, and only differences are described in detail.

As shown in FIG. 10(a), the second cylindrical part 16 has, on a part of the second cylindrical part 16 which extends in a circumferential direction, the reinforcing part 80 as the expansion/contraction limiting part that limits axial expansion/contraction of the second cylindrical part 16. In other words, the second cylindrical part 16 can have, on the surface, the reinforcing part 80 having a prescribed length along the longitudinal direction of the second cylindrical part 16. As shown in FIG. 10(b), the reinforcing part 80 is fixed to a predetermined region on the outer surface of the second cylindrical part 16. Then, as shown in FIG. 10(c), the reinforcing part 80 is fixed to at least a part of a region that becomes outside of a bent part when the second cylindrical part 16 is bent. This can minimize damages of the second cylindrical part 16 even when the second cylindrical part 16 is repeatedly bent.

The reinforcing part 80 is formed by a thin-plate metallic material or resin material. As the metallic material, stainless steel, aluminum alloy, titanium, and/or titanium alloy or the like can be used. Additionally, the reinforcing part 80 can be formed by using a belt-like member made of carbon fibers, aramid fibers or the like. Further, the reinforcing part 80 is fixed on the surface of the second cylindrical part 16, for example, by using spot welding or a bonding member, such as adhesive, suitable for a material forming the reinforcing part 80.

Moreover, the expansion/contraction limiting part can be provided to the second cylindrical part 16d described in FIGS. 7(a) and 7(b). To be more precise, the second cylindrical part 16d can have, on a part of the second cylindrical part 16d in a circumferential direction in an extended state, the reinforcing part 80 as the expansion/contraction limiting part that limits axial expansion/contraction of the second cylindrical part 16d (hereinafter referred to as a "second cylindrical part A"). In other words, the second cylindrical part A has, on the surface, in the extended state, the reinforcing part 80 having a prescribed length along the longitudinal direction of the second cylindrical part 16d. In this case, in a state where the fluid in the first cylindrical part 14 is not pressurized, the second cylindrical part A has flexibility. Consequently, since flexibility is provided to a region including a part asymmetrically corresponding to a part provided with the reinforcing part 80 when an axis of the second cylindrical part A is defined as a symmetric axis, the entire second cylindrical part A is in a state capable of bending with the reinforcing part 80 side being convex. Then, when the fluid in the first cylindrical part 14 is pressurized, the second cylindrical part A is applied with a driving force to be straight in an axial direction.

Additionally, the second cylindrical part 16d can also have, on a part of the second cylindrical part 16d in a circumferential direction in a contracted state, the reinforcing part 80 as the expansion/contraction limiting part that limits axial expansion/contraction of the second cylindrical part 16d (hereinafter referred to as a "second cylindrical part B"). In other words, the second cylindrical part B has, on the surface, in the contracted state, the reinforcing part 80 having a prescribed length along a longitudinal direction of the second cylindrical part B. In this case, pressurization of the fluid in the first cylindrical part 14 causes extension of a region including a part asymmetrically corresponding to a part provided with the reinforcing part 80 when an axis of the second cylindrical part B is defined as a symmetric axis, generating a driving force for bending with the reinforcing part 80 side being concave, in the entire second cylindrical part B.

Thus, the expansion/contraction limiting part provides a function for assisting an action of the driving force of the assisting part 10 in a prescribed direction. The assistance device 1 can include the assisting part 10 having both the second cylindrical part A and the second cylindrical part B. In this case, the second cylindrical part A assists the driving force for the bending action with the side provided with the reinforcing part 80 of the second cylindrical part A being convex, and the second cylindrical part B assists the driving force for the bending action with the side provided with the reinforcing part 80 of the second cylindrical part B being concave. Additionally, the assisting part 10 may also have a plurality of the second cylindrical parts A. In this case, it is also possible to direct either of a reinforcing part 80 of one second cylindrical part A, and a reinforcing part 80 of another second cylindrical part A, to the wearer 5 side. Similarly, the assisting part 10 can have a plurality of the second cylindrical parts B, and it is also possible to direct either of a reinforcing part 80 of one second cylindrical part B, and a reinforcing part 80 of another second cylindrical part B, to the wearer 5 side.

Moreover, the second cylindrical part 16d can also be provided with the expansion/contraction limiting part inside the second cylindrical part. 16d, in a range where the first cylindrical part 14 is not damaged, and the function of the first cylindrical part 14 can be provided. Moreover, the second cylindrical part 16d may be provided with the expansion/contraction limiting part by having structure that substantially limits expansion/contraction along an axial direction, of a part of the second cylindrical part 16d in a circumferential direction. For example, in the second cylindrical part 16d, a part of one small cylindrical part in a circumferential direction is fixed with a part of another small cylindrical part in a circumferential direction, which is adjacent to the one small cylindrical part, and thereby to cause an extended state or a contracted state of the second cylindrical part 16d including a part asymmetrically corresponding to the fixed portion. The one small cylindrical part and the another small cylindrical part can be, for example, fixed by welding. Further, instead of the second cylindrical part 16d, the second cylindrical part 16 can be used as long as it can be axially extended and contracted.

(Raising Part 90)

Figure 11A:
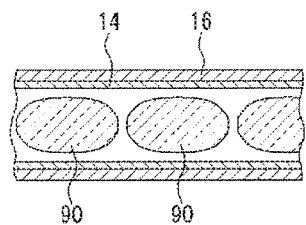
FIGS. 11(a) to 11(c) are outline views of a raising part housed in the first cylindrical part according to the embodiment.
Figure 11B:
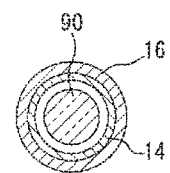
Figure 11C:
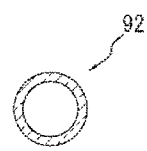

FIGS. 11(a) to 11(c) illustrate an example of an outline of a raising part housed in the first cylindrical part according to the embodiment. FIG. 11(a) illustrates a state where the raising part 90 is housed in the first cylindrical part 14, FIG. 11(b) illustrates an example of a cross section of the first cylindrical part 14 housed with the raising part 90, and FIG. 11(c) illustrates an example of a cross section of the raising part according to a modified example.

The raising part 90 is housed inside the first cylindrical part 14. The first cylindrical part 14 can house a plurality of the raising parts 90 inside. Containing the raising part 90 inside enables reduction of an amount of fluid that flows into the first cylindrical part 14. Consequently, in the assisting part 10 provided with the first cylindrical part 14 containing the raising part 90 inside, a driving time of the assisting part 10 cart be shortened as compared with when the raising part 90 is not contained inside.

The raising part 90 is formed by using a material that does not infiltrate fluid, and is not easily deformed by pressure applied to the fluid. Moreover, the raising part 90 is preferably formed by lasing a material lighter than a specific gravity of fluid used for the assistance device 1. For example, the raising part 90 can be formed by using a resin material such as polypropylene or polyethylene. As an example, when the fluid is water, the raising part 90 is preferably formed by using a material having a smaller specific gravity than the specific gravity of water. Further, the raising part 90 can also be formed, for the purpose of weight reduction, by using resin made by kneading a resin as a base material with an additive with a smaller specific gravity than that of the fluid or the base material. As the additive, for example, hollow glass beads are available. Then, as shown in FIG. 11(b), the raising part 90 has structure without having a cavity. When the raising part 90 has the structure without having a cavity, deformation of the raising part 90 due to pressure can be significantly prevented.

Moreover, the raising part 90 cart also be formed by using a material having a prescribed elasticity. For example, the raising part 90 may be formed by using a material, such as low-foaming plastic, that is deformed to some extent due to pressurization. In this case, when the fluid in the first cylindrical part 14 is pressurized, pressure is applied to the raising part 90 having the prescribed elasticity, and volume of the raising part 90 is slightly decreased. This generates a part through which the fluid flows around the raising part 90, allowing control of flexibility in the entire assisting part 10.

Additionally, the raising part 90 can have various kinds of shapes, such as a spherical shape or a rectangular shape, as long as it has a maximum diameter of a cross section that is equal to or less than an inner diameter of the first cylindrical part 14, and is large enough not to be released outside from an end part (i.e., the inlet 30) of the first cylindrical part 14.

Additionally, as shown in FIG. 11(c), in the modified example, a raising part 92 having a hollow inside can be used. For example, there can be used the raising part 92 in a shape enclosing gas having a prescribed pressure inside (e.g., pressure of about 1 MPa), by using a resin material such as polypropylene. Using the raising part 92 having such a shape enables further reduction of weight of the assistance device 1.

Figure 12A:
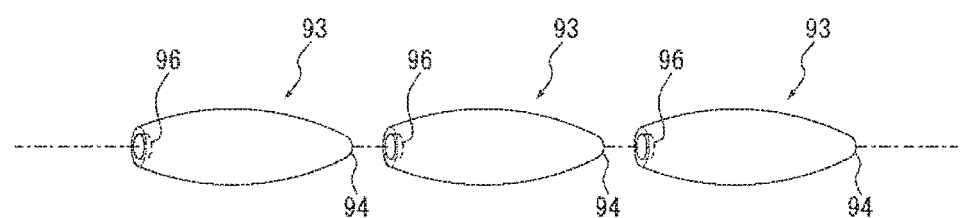
FIGS. 12(a) and 12(b) are outline views of a raising part housed in the first cylindrical part in still other modified examples, according to the embodiment.
Figure 12B:
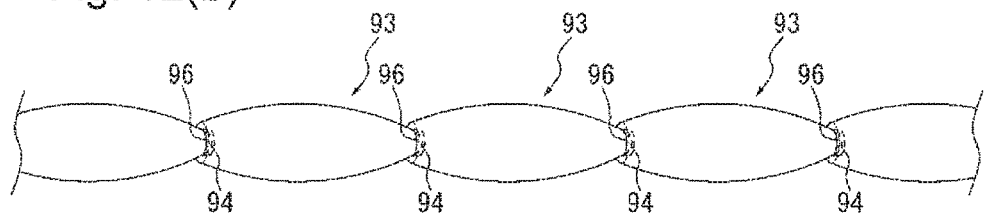

FIGS. 12(a) and 12(b) illustrate outlines of a raising part housed in the first cylindrical part in still other modified examples, according to the embodiment.

The raising part can be configured by combining members of various shapes. For example, there can be used a raising part 93 having a convex-spherical-surface part 94 machined into a convex spherical surface at a first end part, and a concave-spherical-surface part 96 machined into a concave spherical surface at a second end part. Then, a plurality of the raising parts 93 can be arranged such that a convex-spherical-surface part 94 of one raising part 93, and a concave-spherical-surface part 96 of a raising part 93 next to the one raising part 93 are made to face and be adjacent to each other as shown in FIG. 12(a), or in contact with each other. Such an arrangement can prevent a center axis of the raising part 93 from shifting and moving in bending of the assisting part 10, which can realize a smooth bending action of the assisting part 10. Additionally, as shown in FIG. 12(b), it is also possible to configure such that a convex-spherical-surface part 94 of one raising part 93 and a concave-spherical-surface part 96 of a raising part 93 next to the one raising part 93 are fitted and coupled to each other.

(Other Shapes of Assisting Part)

Figure 13A:
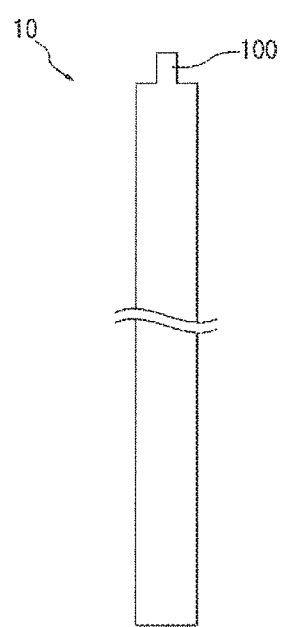
FIGS. 13(a) and 13(b) are views of a shape of the assisting part according to the embodiment.
Figure 13B:
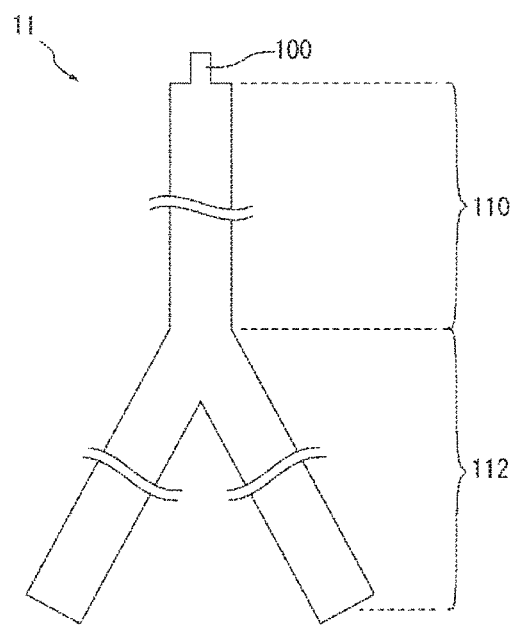

FIGS. 13(a) and 13(b) illustrate examples of a shape of the assisting part according to the embodiment.

First, as shown in FIG. 13(a), the assisting part 10 can be formed into a single piece shape. In this case, the assisting part 10 is formed to have a substantially cylindrical shape. Additionally, as shown in FIG. 13(b), in another embodiment, the assisting part 11 can be configured to be divided into a plurality of portions. For example, the assisting part 11 can be configured to have an upper assisting part 110 and a lower assisting part 112. The upper assisting part 110 is configured to have a length corresponding to a back surface of the wearer 5. Further, the lower assisting part 112 is configured to be forked from an end part of the upper assisting part 110, which corresponds to the vicinity of the lower back portion of the wearer 5, and to extend to the vicinity of the upper knee portion 22.

(Detail of Assist-Control Unit)

Figure 14:
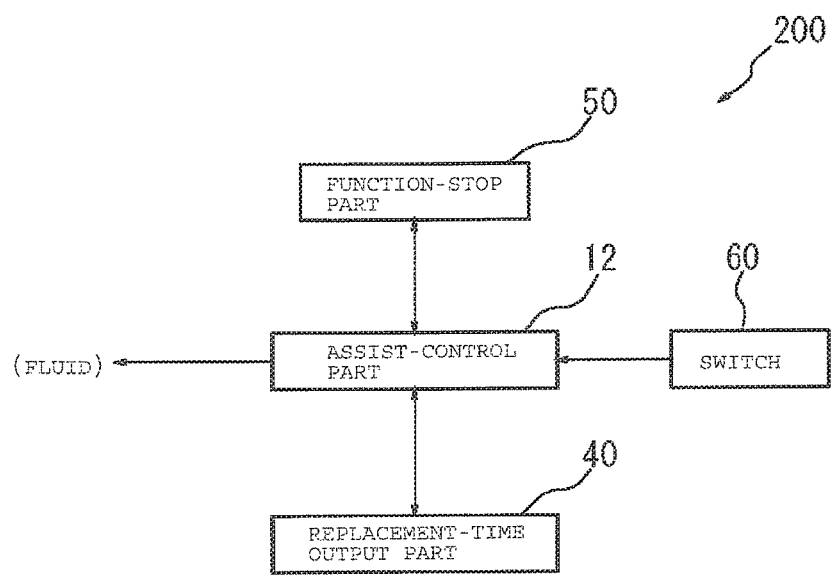
FIG. 14 is a functional-configuration block diagram of an assist-control unit according to the embodiment.

FIG. 14 shows an example of functional configuration of an assist-control unit according to the embodiment.

An assist-control unit 200 is a unit that controls flexibility of the assisting part 10. The assist-control unit 200 has an assist-control part 12 that controls flexibility of the assisting part 10; a replacement-time output part 40 that outputs a replacement time of the assisting part 10; a function-stop part 50 that stops a prescribed function of the assistance device 1 when an abnormality or the like occurs in the assisting part 10; and a switch 60 that makes the assist-control part 12 execute pressurization or decompression of fluid, or retention of the pressure. Moreover, the assist-control part 12 may include a part or all of functions and/or configurations of the replacement-time output part 40, the function-stop part 50, and the switch 60.

The assist-control part 12 is configured to have, as the pressure-control part, a pump for liquid-pressure feeding that allows incompressible fluid to flow in and out of the first cylindrical part 14. The assist-control part 12 is connected to a first end of the assisting part 10. Then, the assist-control part 12 executes pressurization or decompression of fluid in the first cylindrical part, or retention of the pressure. Moreover, the assist-control part 12 can allow the fluid to flow in and out of the first cylindrical part as it is, or can allow the fluid flow into the first cylindrical part by supplying the fluid into the first cylindrical part that has been decompressed to a prescribed pressure.

As the switch 60, various forms of a switch, such as a mechanical switch or an electronic switch, can be used. For example, the switch 60 can be a mechanical switch that allows the wearer 5 to perform ON/OFF by tilting his/her head. In this case, the switch 60 is preferably provided near a shoulder of the assistance garment 2. Additionally, as the switch 60, a voice switch, a line-of-sight switch, or an exhalation switch can also be used.

When a degree of deterioration of the assisting part 10, which is determined based on a number of times that the flexibility of the assisting part 10 has been changed by the assist-control part 12, has exceeded a predetermined reference, or when the degree of deterioration is included within a prescribed range from the predetermined reference, the replacement-time output part 40 perceivably outputs that assisting part 10 has reached its replacement time, or may reach the replacement time within a prescribed period, to a user such as the wearer 5. The replacement-time output part 40 can include a number-of-times measurement part that measures a number of bending of the assisting part 10; a pressure detection part that detects pressure applied to the assisting part 10 in bending of the assisting part 10; an angle detection part that detects a bending angle in bending of the assisting part 10; and/or an information-holding part that holds information indicating a measurement content or a detection content of the number-of-times measurement part, the pressure detection part, and the angle detection part, or the like.

Here, the degree of deterioration is an extent of deterioration of the assisting part 10, which is predicted based on a number of bending, a pressurizing pressure in bending, and/or a bending angle or the like, of the assisting part 10. For example, the replacement-time output part 40 perceivably outputs the replacement time of the assisting part 10 to a user such as the wearer 5, when the number of bending has exceeded a predetermined number, or a product of the number of bending of the assisting part 10 and an average value of the pressure applied to the assisting part 10 has exceeded a predetermined value, or the like. The replacement-time output part 40 outputs the replacement time through a sound or an alarm tone to notify the replacement time. Additionally, the replacement-time output part 40 can include a light-emitting part, and can also output the replacement time by making the light-emitting part emit light in a predetermined light-emitting pattern, along with the sound or the alarm tone, or separately from the sound or the alarm tone. Further, the replacement-time output part 40 resets the information held by the information-holding part, when the assisting part 10 is replaced. Moreover, the replacement-time output part 40 may output information indicating the replacement time as data.

Additionally, the replacement-time output part 40 can include a replacement-time transmission part that transmits, to an external server, an information processing terminal or the like, time information indicating that the assisting part 10 has reached the replacement time and/or may reach the replacement time within a prescribed period (i.e., becoming close to the replacement time, more specifically, the degree of deterioration has become to be included within a prescribed range from the predetermined reference). The external server is, for example, a server owned by a provider providing the assistance device 1, a server of a manager managing use of the assistance device 1, or the like. The information processing terminal is, for example, an information processing terminal owned by a provider providing the assistance device 1, an information processing terminal of a manager managing use of the assistance device 1. The external server, the information processing terminal or the like receives time information from the replacement-time transmission part, and grasps the replacement time of the assisting part 10 based on the received time information.

The replacement-time transmission part transmits time information to the external server, the information processing terminal or the like, for example, through wired or wireless communication, via a wired or wireless LAN, or a communication network such as the Internet or a cellular phone network. The replacement-time transmission part can communicate with the external server, the information processing terminal or the like, constantly during operation of the assistance device 1, or at a predetermined interval during the operation of the assistance device 1. Additionally, the replacement-time transmission part can also record the time information on an information recording medium, such as a semiconductor memory. When the replacement-time transmission part records the time information on the information recording medium, the external server, the information processing terminal or the like receives time information from the information recording medium, thereby to grasp the replacement time of the assisting part 10.

The function-stop part 50 stops a function of the assist-control part 12 when the replacement-time output part 40 outputs the replacement time, and/or an abnormality has occurred in the assist-control part 12. This allows operation of the assist-control part 12 to be stopped even when the switch 60 becomes ON, which can prevent damage of the assisting part 10.

An example of operation of the assist-control unit 200 having the configuration above is as follows. First, the switch 60 is turned to ON, so that the assist-control part 12 starts operation. In other words, the assist-control part 12 starts the operation for allowing fluid to flow into the first cylindrical part 14. This causes the assist-control part 12 to change (i.e., reduce) flexibility of the assisting part 10, to apply force for assisting an action of the wearer 5 to the body of the wearer 5. On the other hand, when the switch 60 is turned to OFF, or when a function of discharging fluid from inside the first cylindrical part 14 is turned ON, the assist-control part 12 increases flexibility of the assisting part 10, to make the assisting part 10 in a flexible state.

[Detail of Assistance Garment 2]

As shown in FIGS. 1(a) and 1(b), the assistance garment 2 according to the embodiment is a garment provided with the assistance device described above. For example, when reducing a burden on the lower back of the wearer 5, the assistance device 1 is provided over the back portion 20 to an upper thigh portion of the assistance garment 2.

The assistance garment 2 includes a holding part 24 that holds a first-end side of the assisting part 10 provided to the assistance device 1, and a fixing part 26 that detachably/attachably fixes a second-end side of the assisting part 10 to the assistance garment 2. The assistance garment 2 may be either of a garment in which an upper half and a lower half of the body are integrated, or a garment in which the upper half and the lower half of the body are separated.

The holding part 24 holds the assisting part 10 in a movable state with respect to the assistance garment 2. For example, the holding part 24 has structure in which a prescribed region including the first end of the assisting part 10 easily slides against a surface of the assistance garment 2, to hold the assisting part 10. As an example, when the assisting part 10 is substantially cylindrical, the holding part 24 has an annular shape that has a larger diameter than a cross sectional diameter of the assisting part 10 (when the assisting part 10 is substantially prismatic or substantially polygonal columnar, a diameter of a circumscribed circle of a cross section of these), and is capable of inserting with the assisting part 10. The holding part 24 is formed by using a same fiber material as that of the assistance garment 2, or a material with a low possibility of damaging a body or an surrounding article or the like even when coming into contact with the body, or the article (e.g., a resin material having flexibility, or the like).

The fixing part 26 detachably/attachably fixes a part of the assisting part 10 to the assistance garment 2. For example, the fixing part 26 is configured to have a hook and loop fastener, a slide fastener, and/or button or the like. For example, when a hook and loop fastener is used as the fixing part 26, a loop surface (or a hook surface) of the hook and loop fastener is provided on the assistance garment 2, and a hook surface (or a loop surface) of the hook and loop fastener is provided on at least a part of a surface of the assisting part 10. Then, a part of the assisting part 10 is fixed to the assistance garment 2, by bringing the hook surface (or the loop surface) of the assisting part 10 into contact with the loop surface (or the hook surface) of the assistance garment 2.

Further, when a slide fastener is used as the fixing part 26, the assistance garment 2 is provided with structure that covers at least a part of the assisting part 10. For example, the assistance garment 2 is provided with a first covering part that covers a part of the assisting part 10 along a longitudinal direction of the assisting part 10, and a second covering part that covers a part of the assisting part 10 along the longitudinal direction of the assisting part 10, at a position opposite to the first covering part, and the slide fastener is provided at an end part on long side of the first covering part, and at an end part on long side of the second covering part. Then, a part of the assisting part 10 is substantially fixed to the assistance garment 2 by closing the slide fastener with a part of the assisting part 10 covered by the first covering part and the second covering part. In this case, at least a part of the assisting part 10 cannot be visually recognized from outside.

Effect of Embodiment

Since the assistance device 1 according to the embodiment is configured such that the assisting part 10 is detachable from and attachable to the assistance garment 2, the assisting part 10 can be replaced as one body. In other words, in the assistance device 1 according to the embodiment, since the assisting part 10 as a main component can be collectively replaced, even when the assisting part 10 is possibly deteriorated after providing the assistance device 1 and the assistance garment 2, the assistance device 1 and the assistance garment 2 need not to be entirety replaced. Since the assistance device 1 and the assistance garment 2 need not to be entirety replaced, user cost can be reduced. Further, since it is not necessary to excessively require durability of the assisting part 10, manufacturing cost can also be reduced.

Additionally, the assistance device 1 reduces a load in an action of the wearer 5 by controlling flexibility of the assisting part 10. Consequently, unlike the conventional art that lifts a body by applying a load to a part of the body with a belt or the like, the assistance device 1 does not apply a load to a body, which can significantly reduce fatigue of the wearer 5. Further, the assistance device 1 can cover at least a part of the assisting part 10, which can prevent damage to a care-receiver or a helped person, or furniture, items or the like around the wearer 5, even when the assisting part 10 comes into contact with these persons or items.

Moreover, the assistance garment 2 is configured as the garment provided with the assistance device 1, the wearer 5 can easily putting on and taking off the assistance garment 2. Furthermore, the assistance garment 2 can cover at least a part of the assisting part 10 (i.e., can prevent at least a part of the assisting part 10 from being visually recognized from outside), which can prevent a person from feeling intimidated when the person sees the wearer 5 wearing the assistance garment 2.

Although the embodiment of the present invention has been described above, the above-described embodiment is not intended to limit the invention according to claims. Further, it should be noted that all the combinations of features described in the embodiment is not always essential for means to solve the problem of the invention. Furthermore, a technical element of the above-described embodiment may be individually applied, or can be divided into a plurality of portions to be applied.

REFERENCE SIGNS LIST 1 assistance device
2 assistance garment
5 wearer
10, 10a, 10b, 10c assisting part
11 assisting part
12 assist-control part
14 first cylindrical part
14a end part
16, 16a, 16b, 16c, 16d, 16e second cylindrical part
20 back portion
22 knee portion 24 holding part
26 fixing part
30, 30a, 30b, 30c, 30d inlet
32, 32a, 32b, 32c, 32d, 32e, 32f sealing part
34 connection part
36 parallel connection part
40 replacement-time output part
50 function-stop part
60 switch
70, 72 receiving part
70a, 72a contact part
80 reinforcing part
90, 92, 93 raising part
94 convex-spherical-surface part
96 concave-spherical-surface part
97 gap
100, 100a, 100b, 100c connection port
102 second end
110 upper assisting part
112 lower assisting part
120 connecting member
140, 140a thin-type cylindrical part
160, 162, 164 cross section
166 front face
168 side face
170 arrow
180, 182, 184, 186 small cylindrical part
190 combination part
200 assist-control unit

The invention claimed is:

1. An assistance device that is provided on a garment and reduces a load of an action of a wearer, the assistance device comprising:
an assisting part that is removeable from the garment, replaceable and applies force for assisting the action to a body of the wearer by changing longitudinal flexibility of the assisting part without causing a shape change in a cross-sectional direction; and
an assist-control part that controls the longitudinal flexibility of the assisting part.

2. The assistance device according to claim 1, wherein the assisting part has a first cylindrical part through which fluid flows in and out, and a second cylindrical part disposed with the first cylindrical part inside the second cylindrical part, and
the assist-control part controls the flexibility of the assisting part by changing pressure of the fluid in the first cylindrical part.

3. The assistance device according to claim 2, wherein the second cylindrical part has higher longitudinal flexibility than radial flexibility, and
the assist-control part increases pressure in the first cylindrical part by pressurizing the fluid, and reduces the flexibility of the assisting part.

4. The assistance device according to claim 2, further comprising a receiving part that is provided inside the second cylindrical part, between an end part of the second cylindrical part and an end part of the first cylindrical part.

5. The assistance device according to claim 2, wherein at least a part of the second cylindrical part is formed from a material with lower flexibility than that of the first cylindrical part.

6. The assistance device according to claim 2, further comprising, between the assist-control part and the first cylindrical part, a state-setting part that sets a state of pressure in the first cylindrical part to a plurality of states.

7. The assistance device according to claim 2, wherein the second cylindrical part has, on a part of the second cylindrical part which extends in a circumferential direction, an expansion/contraction limiting part that limits axial expansion/contraction of the second cylindrical part.

8. The assistance device according to claim 2, wherein the fluid is incompressible fluid.

9. The assistance device according to claim 1, further comprising a replacement-time output part that outputs that the assisting part has reached a replacement time thereof or the assisting part may reach the replacement time within a prescribed period, when a degree of deterioration of the assisting part has reached a predetermined reference, or when the degree of deterioration is included within a prescribed range from the predetermined reference, wherein the degree of deterioration is determined in accordance with a number of times that the flexibility of the assisting part has been changed by the assist-control part.

10. The assistance device according to claim 9, wherein the replacement-time output part includes a replacement-time transmission part that transmits time information indicating that the replacement time has been reached, or may be reached within a prescribed period.

11. An assistance garment provided with an assistance device that is provided on a garment and reduces a load in an action of a wearer on a back portion, the assistance device having an assisting part that is removeable from the garment, replaceable and applies force for assisting the action to a body of the wearer by changing longitudinal flexibility of the assisting part without causing a shape change in a cross-sectional direction, and an assist-control part that controls the longitudinal flexibility of the assisting part, the assistance garment comprising:
a holding part that is inserted with a first-end side of the assisting part and holds the first-end side movably along a longitudinal direction of the back portion; and
a fixing part that detachably/attachably fixes at least a part of the assisting part other than the first-end side, to the assistance garment.

12. The assistance garment according to claim 11, wherein the assisting part has a first cylindrical part through which fluid flows in and out and a second cylindrical part disposed with the first cylindrical part inside, and the assist-control part controls the flexibility of the assisting part by changing pressure of the fluid in the first cylindrical part.

13. The assistance garment according to claim 11, wherein the fixing part detachably/attachably fixes a second-end side of the assisting part at a position of a knee portion or higher, of the assistance garment.

14. The assistance garment according to claim 11, wherein the fixing part covers at least a part of the assisting part.

15. An assistance method for operating an assistance device that is provided on a garment and reduces a load in an action of a wearer, the assistance method comprising:
an assist-control step for controlling longitudinal flexibility of an assisting part that is removeable from the garment, replaceable and applies force for assisting the action to a body of the wearer by changing the longitudinal flexibility without causing a shape change in a cross-sectional direction.

16. The assistance method according to claim 15, wherein the assisting part has a first cylindrical part through which fluid flows in and out, and a second cylindrical part disposed with the first cylindrical part inside, and the assist-control step controls the flexibility of the assisting part by changing pressure of the fluid in the first cylindrical part.

17. The assistance method according to claim 16, wherein the second cylindrical part has higher longitudinal flexibility than radial flexibility, and in the assist-control step, pressure in the first cylindrical part is increased by pressurizing the fluid, and the flexibility of the assisting part is reduced.

\* \* \* \* \*